US009844673B2

(12) United States Patent
Koubeissi et al.

(10) Patent No.: US 9,844,673 B2
(45) Date of Patent: *Dec. 19, 2017

(54) STIMULATION OF THE FORNO-DORSO-COMMISSURE (FDC) FOR SEIZURE SUPPRESSION AND MEMORY IMPROVEMENT (71) Applicant: CASE WESTERN RESERVE UNIVERSITY, Cleveland, OH (US)

(72) Inventors: Mohamad Koubeissi, Cleveland, OH (US); Dominique Durand, Cleveland, OH (US); Jonathan Miller, Cleveland, OH (US); Hans Luders, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/281,548

(22) Filed: Sep. 30, 2016

(65) Prior Publication Data
US 2017/0014626 A1 Jan. 19, 2017

Related U.S. Application Data (63) Continuation of application No. 14/761,343, filed as application No. PCT/US2014/011872 on Jan. 16, 2014, now Pat. No. 9,486,634.
(Continued)

(51) Int. Cl.
*A61N 1/00* (2006.01)
*A61N 1/36* (2006.01)
(Continued)

(52) U.S. Cl.
CPC ........ *A61N 1/36064* (2013.01); *A61B 5/0484* (2013.01); *A61N 1/0534* (2013.01);
(Continued)

(58) Field of Classification Search
CPC .............. A61N 1/36139; A61N 1/0534; A61N 1/36082
See application file for complete search history.

(56) References Cited

U.S. PATENT DOCUMENTS

2002/0077670 A1 6/2002 Archer
2003/0028072 A1* 2/2003 Fischell .................. A61N 1/32
600/13
(Continued)

OTHER PUBLICATIONS

International Search Report and Written Opinion for PCT/US2014/011872, dated Mar. 24, 2014, pp. 1-4.
(Continued)

*Primary Examiner* — Robert N Wieland
(74) *Attorney, Agent, or Firm* — Tarolli, Sundheim, Covell & Tummino LLP (57) ABSTRACT Example apparatus and methods cause activation of target neural tissue through electrical stimulation of a connected white matter tract to reduce the hyper-excitability of the target neural tissue and thus reduce seizures while preserving memory in humans. Example apparatus and methods apply low frequency (e.g., <10 HZ) electrical stimulation to the forno-dorso-commissure (FDC), detect an electrical signal generated in an area connected to, innervated by, or that can be activated by the FDC in response to the stimulation, and reconfigure the stimulation based on the detected signal and a desired therapeutic effect. The stimulation may be reconfigured to produce an electrical stimulation waveform that will produce the desired therapeutic effect. The desired therapeutic effect may be, for example, reducing hyper-excitability of neural tissue in a target area, reducing hippocampal spikes, reducing seizure odds, or improving recall.

20 Claims, 6 Drawing Sheets

Related U.S. Application Data

(60) Provisional application No. 61/753,503, filed on Jan. 17, 2013, provisional application No. 61/912,378, filed on Dec. 5, 2013.

(51) Int. Cl.
*A61B 5/0484* (2006.01)
*A61N 1/05* (2006.01)

(52) U.S. Cl.
CPC ..... *A61N 1/36082* (2013.01); *A61N 1/36092* (2013.01); *A61N 1/36139* (2013.01); *A61N 1/36171* (2013.01)

(56) References Cited

U.S. PATENT DOCUMENTS

| | | |
|---|---|---|
| 2003/0087264 A1 | 5/2003 | Kaplitt |
| 2005/0010261 A1 | 1/2005 | Luders et al. |
| 2005/0049649 A1 | 3/2005 | Luders et al. |
| 2007/0067003 A1 | 3/2007 | Sanchez |
| 2007/0142874 A1 | 6/2007 | John |
| 2007/0213786 A1 | 9/2007 | Sackellares |
| 2008/0004660 A1 | 1/2008 | Assaf et al. |
| 2009/0030480 A1 | 1/2009 | Durand |

OTHER PUBLICATIONS

Canadian Office Action for corresponding PCT/US2014/011872, dated Sep. 23, 2016, pp. 1-3.

\* cited by examiner

STIMULATION OF THE FORNO-DORSO-COMMISSURE (FDC) FOR SEIZURE SUPPRESSION AND MEMORY IMPROVEMENT

CROSS REFERENCE TO RELATED APPLICATIONS

This application is a continuation of U.S. application Ser. No. 14/761,343, filed Jul. 16, 2015 (now U.S. Pat. No. 9,486,634), and entitled "STIMULATION OF THE FORNO-DORSO-COMMISSURE (FDC) FOR SEIZURE SUPPRESSION AND MEMORY IMPROVEMENT", which is a national stage entry of PCT/US14/11872, filed Jan. 16, 2014, which claims the benefit of U.S. Provisional Application 61/753,503 filed Jan. 17, 2013 and U.S. Provisional Application 61/912,378 filed Dec. 5, 2013.

BACKGROUND

Temporal lobe epilepsy is the most common focal epilepsy in adolescents and adults, and the most frequent indication for epilepsy surgery. Mesial temporal lobe epilepsy (MTLE) often originates from the hippocampus, which is implicated in declarative memory function. A clinical trial in patients with intractable MTLE showed that temporal lobectomy is superior to continued medical therapy in achieving seizure freedom. However, resection is generally eschewed if pre-surgical evaluation predicts functional deficits. Additionally, more than half of all intractable patients are not candidates for surgical resection. The risk of memory decline after hippocampal resection depends on the structural integrity of the hippocampus and its degree of contribution to memory function prior to surgery. A non-lesional, language dominant hippocampus and good preoperative memory function often exclude MTLE patients from temporal lobectomy because of the high-risk of postoperative memory decline. This underlies the need to pursue controlling disabling hippocampal seizures without compromising memory function.

While surgical resection of the temporal lobe is an effective treatment for medically-intractable temporal lobe epilepsy, surgical resection often results in memory impairment. Thus, other approaches including deep brain stimulation (DBS) have been undertaken. DBS in epilepsy has targeted gray matter structures using high frequencies, but has not achieved desired results. Conventional DBS may provide a first stimulation when there is no prediction of an impending seizure but may provide a second altered stimulation based on a prediction of an impending seizure, where the prediction is based on monitoring naturally occurring, organically generated signals. For example, conventional systems may be programmed to detect and record seizure activity based on signals generated naturally in the brain by the brain itself. Conventional systems may also be configured to control stimulation as a function of the detected or recorded seizure activity.

DBS has risen as an effective treatment in patients with movement or psychiatric disorders. The stimulation targets specific areas in the brain, altering the function of circuits or inducing neurogenesis and other plastic changes. DBS has been approved for treatment of Parkinson's disease, essential tremor, dystonia, and obsessive-compulsive disorder, but its success in epilepsy has been limited. Most stimulation trials in epilepsy have used high frequencies.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Example apparatus and methods cause activation of target neural tissue (e.g., amygdala, hippocampus, posterior cingulate gyrus) through electrical stimulation of a connected white matter tract. The stimulation and resulting evoked response reduce the hyper-excitability of the target neural tissue which may in turn reduce interictal epileptiform discharges and seizures while preserving memory in humans. Example apparatus and methods apply low frequency (e.g., <10 HZ) electrical stimulation to the forno-dorso-commissure (FDC) in patients implanted with depth electrodes, detect an electrical signal generated in response to the stimulation, and reconfigure the stimulation based on the detected signal and a desired therapeutic effect. The electrical signal is detected in a target area that is connected to the stimulated white matter, innervated by the stimulated white matter, or that can be activated by stimulating the white matter.

Surgical resection of the temporal lobe is an effective treatment for medically-intractable temporal lobe epilepsy, but often results in memory impairment. Deep brain stimulation (DBS) to treat epilepsy has targeted gray matter structures using high frequencies. But high frequencies have not produced desired results and may produce undesired side-effects. Experiments in animals have shown that low frequency stimulation can delay epileptogenesis. Experiments have also shown that low frequency stimulation applied to a white matter tract can reduce seizure in different animal models of MTLE. Thus, example methods and apparatus concern low-frequency stimulation of white matter (e.g., FDC) to reduce hyper-excitability of target neural tissues which may in turn reduce interictal epileptiform discharges and seizures in patients with intractable mesial temporal lobe epilepsy. After stimulating white matter, a resulting electrical signal is measured in a target area in the brain. The target area is connected to, innervated by, or can be activated by the white matter. The resulting electrical signal is not a naturally occurring signal but rather is caused by and is a function of the stimulation.

Conventional stimulation studies in epilepsy have used high-frequencies of 100-165 Hz and found limited benefit in reducing seizures. Possible mechanisms of action of high-frequency stimulation include activation of presynaptic inhibitory inputs and activation of efferent projections, reducing deleterious signals in neural circuits by reducing "information content" Activation of efferent projections may affect the proper functioning of the stimulated brain structure and produce alterations in memory processing observed during direct stimulation of the hippocampus at either high or low frequencies. Direct hippocampal stimulation is spatially limited and results in only limited benefit as regards seizure reduction. But direct hippocampal stimulation has been shown to interfere with memory processing at either high or low frequencies. Unlike direct hippocampal stimulation, stimulation of hippocampal afferents may produce fewer disruptive effects on memory because afferent tract stimulation spares hippocampal interneurons and glia from direct activation. Instead, afferent tract stimulation activates a homogeneous neuronal population, such as dentate granule cells, as with entorhinal stimulation, or pyramidal cells, as in fornix stimulation. Low frequency stimulation can inhibit abnormal excitatory activity by increasing the threshold of action potential firing by long term depression, or increasing gamma-aminobutyric acid (GABA) mediated inhibition. These mechanisms are different from those of high frequency stimulation, and may not only reduce seizures, but remodel the tissue in a manner that improves functional deficits related to the epileptogenicity of a particular brain region. Indeed, low-frequency stimulation of either the kindling focus or areas that participate in seizure spread delays seizure development in a hippocampal epilepsy model in rats. Even in fully kindled animals, preemptive low frequency stimulation at the hippocampal commissure dramatically decreases stage 5 seizures.

Figure 6:
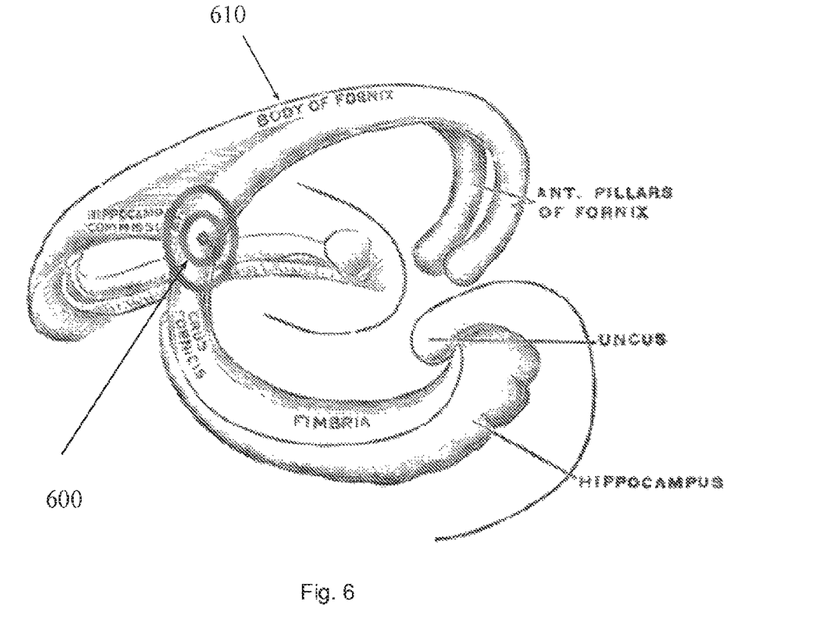
FIG. 6 illustrates the location of an FDC.

Example apparatus and methods treat patients suffering from epilepsy. In one embodiment, apparatus and methods may treat mesial temporal lobe epilepsy. Experiments in human patients have shown that stimulation at the FDC reduces interictal epileptiform discharges and seizures in patients with intractable mesial temporal lobe epilepsy. The reduction may be due to increasing a threshold of action potential firing in the neural tissue in the target area by long term depression, or by increasing GABA-mediated inhibition in the neural tissue in the target area. The FDC is an area that is anterolateral to the splenium of the corpus callosum where the crux of the fornix travels with fibers of the dorsal hippocampal commissure. In one embodiment, an electrode is located as shown in FIG. 6. In different embodiments, a single electrode may be placed unilaterally or two electrodes may be placed bilaterally.

Figure 1:
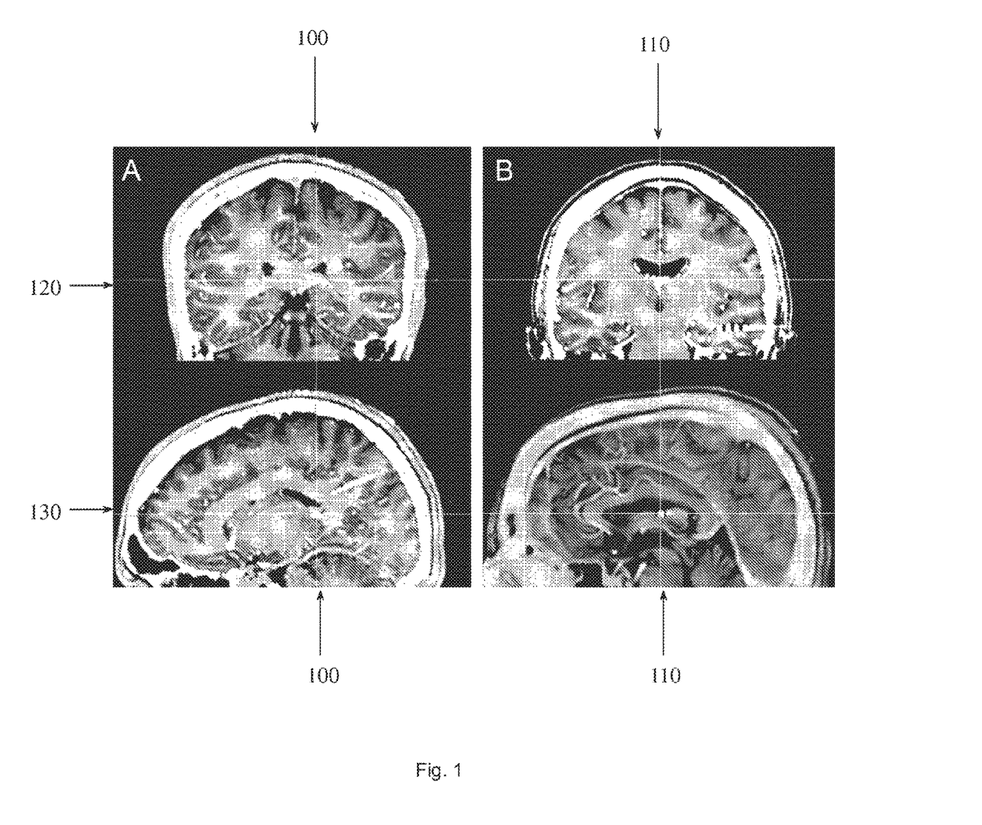
FIG. 1 illustrates a pre-operative brain magnetic resonance imaging (MRI) image co-registered with a postoperative computed tomography (CT) scan showing the location of depth electrodes in the forno-dorso-commissural (FDC) tract and the body of the fornix.

FIG. 1 illustrates a pre-operative brain MRI co-registered with postoperative CT scan showing the location of depth electrodes in the forno-dorso-commissural tract at the intersection of lines 100 and 120 and lines 110 and 130. FIG. 1 also shows the location of depth electrodes in the body of the fornix at the intersection of lines 110 and 120 and at the intersection of lines 110 and 130.

Figure 2A:
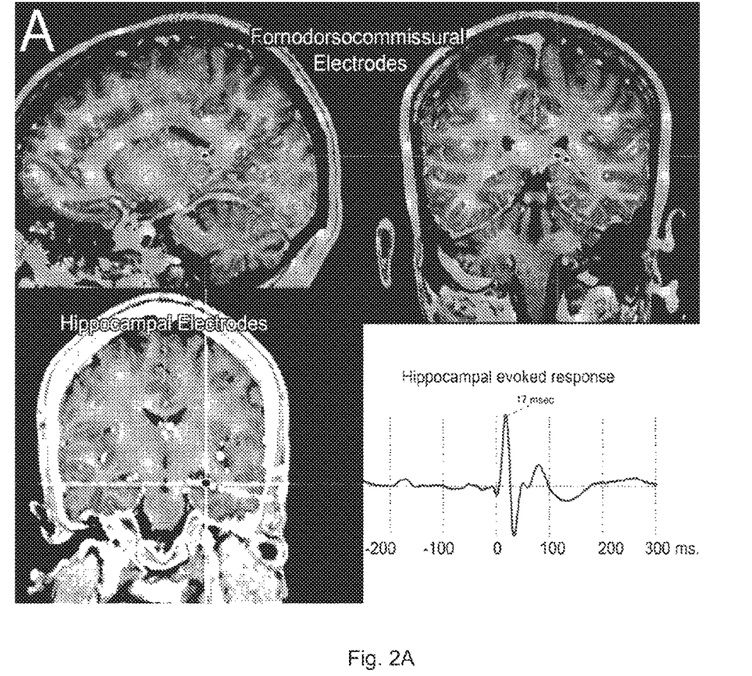
FIG. 2A illustrates locations of forno-dorso-commissural electrodes in a subject in sagittal and coronal views where 1 Hz stimulation was applied, a hippocampal electrode where the evoked response was recorded, and a graph of a hippocampal evoked response.

FIG. 2A provides sagittal and coronal views of locations of the forno-dorso-commissural electrodes in a subject. The electrodes include an electrode in the FDC where 1 Hz stimulation was done and the hippocampal electrode where an evoked response was monitored. A hippocampal evoked response is shown at 17 msec following 1 Hz stimulation.

Figure 2B:
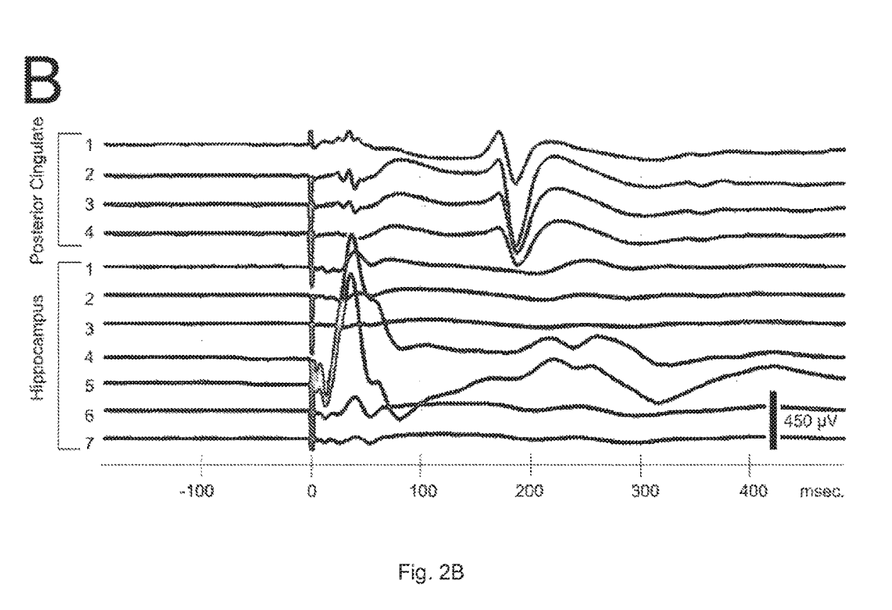
FIG. 2B illustrates evoked potentials detected in the hippocampus and posterior cingulate gyms, with respective peaks at 36 and 187 msec, in response to a 1-Hz stimulation of the fornix.

FIG. 2B illustrates evoked potentials recorded in the hippocampus and posterior cingulate gyrus. Potentials may be recorded in other target areas (e.g., amygdala). FIG. 2B shows peaks at 36 msec for the potential evoked in the hippocampus and peaks at 187 msec for the potential evoked in the posterior cingulate gyrus. The peaks were produced using 1-Hz stimulation of the fornix.

Figure 2C:
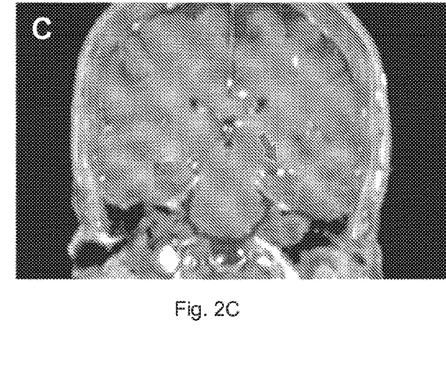
FIG. 2C is a coronal MRI that shows the location of an electrode in the hippocampal body where responses with maximal voltages were recorded.

FIG. 2C is a coronal MRI that shows the location of an electrode in the hippocampal body where responses with maximal voltages were recorded after stimulation performed using the electrode illustrated in FIG. 2A.

Figure 2D:
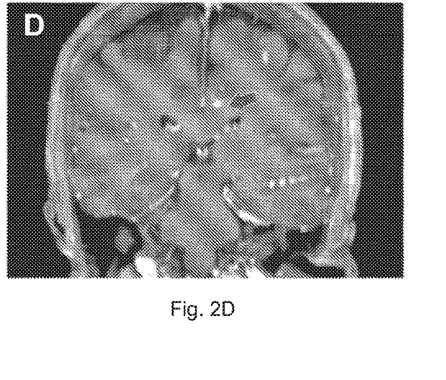
FIG. 2D is a coronal MRI that shows the location of an electrode in the posterior cingulate gyms where responses with maximal voltages were recorded.

FIG. 2D is a coronal MRI that shows the location of an electrode in the posterior cingulate gyrus where responses with maximal voltages were recorded after stimulation performed using the electrode illustrated in FIG. 2A.

The fornix has approximately 1.2 million fibers. These include fibers that originate in the hypothalamus and other subcortical structures and that terminate in the hippocampus and parahippocampus. The fornix also includes fibers that travel in the opposite direction, originating in the subiculum, CA3 region of the hippocampus, entorhinal cortex, and parahippocampal gyrus. The fornix enables the transmission of information ascending to the brainstem to influence the functioning of the limbic system, and may mediate some of the autonomic symptoms of MTLE seizures by connecting the hippocampus with the hypothalamus. The role of the fornix in memory is well-established. For example, high frequency stimulation of the fornix results in vivid recollection of past events, and bilateral fornicotomy causes amnesia.

In different experiments, depth electrodes were implanted in patients in the FDC for surgical evaluation of intractable epilepsy. Low frequency stimulation occurred in four-hour sessions. In different examples, stimulation may be performed in sessions of different duration. During a session, the stimulation was provided continuously at an application frequency (e.g., 1 Hz). Mental status assessment was performed at baseline and during stimulation. The effect of stimulation on hippocampal spikes and seizures was measured.

Stimulation of the FDC elicited evoked responses in the hippocampus and the posterior cingulate gyrus. Responses may also be evoked in other areas (e.g., amygdala). Hourly mini-mental status examination scores showed an increase during stimulation, largely due to improvement in recall. Hippocampal spikes were reduced during and outlasting each stimulation session.

Figure 5:
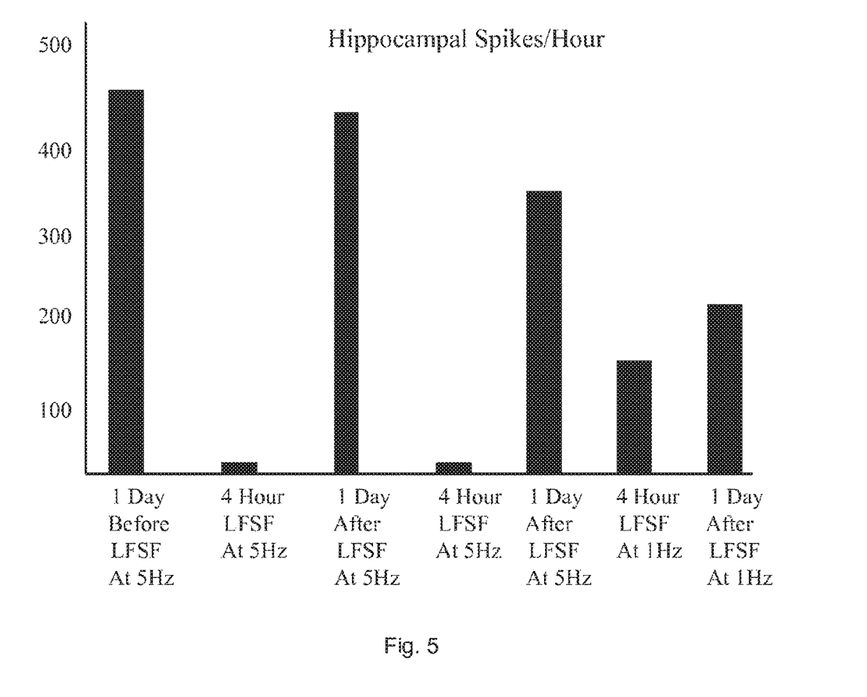
FIG. 5 illustrates results from a series of stimulation sessions for a patient.

FIG. 5 illustrates hippocampal spikes per hour for a patient during and after stimulation with different frequency. The reduction in seizures and hippocampal spikes are the result of reducing the hyper-excitability of neural tissue that is innervated by, connected to, or activated by the stimulation site.

Stimulation of the FDC tract site activates the hippocampus and other areas of the declarative memory circuit and default mode network. Stimulation of the FDC is tolerable and reduces epileptiform discharges and seizures in patients with intractable mesial temporal lobe epilepsy. In one embodiment, FDC tract stimulation may improve memory in patients with Alzheimer's disease, hippocampal sclerosis, autism, schizophrenia or stroke. In another embodiment, FDC tract stimulation may improve memory in patients with memory disorders including, but not limited to, psychiatric or cognitive disorders and senile dementia.

Fornix stimulation elicited evoked responses in the hippocampus and the posterior cingulate gyrus. Thus, example systems and methods monitor responses evoked by stimulation rather than making predictions based on naturally occurring signals. Stimulation of the white matter tract may be done by placing an electrode directly into the tract and stimulating. The amplitude of the stimulus can be adjusted and the amplitude of the stimulation produced may be monitored or recorded. For example, an evoked potential in a connected area may be monitored or recorded. In different embodiments, the stimulus can be adjusted to generate between zero percent and one hundred percent of the evoked potential amplitude necessary to generate a desired therapeutic effect. The stimulus can be adjusted. For example, a monitoring or recording electrode may be located in a target nucleus innervated by the white matter tract being stimulated. A feedback loop may be established to control the stimulation level. The stimulation level may be adjusted to control the amplitude of the evoked potential during the stimulation period to maintain or achieve the desired therapeutic outcome. The stimulation level may be controlled by adjusting the current, voltage, or other parameter (e.g., waveform) of the stimulation.

Example apparatus and methods may be decoupled from directly detecting or recording seizure activity based on naturally occurring signals generated by the brain. Instead, example apparatus and methods may control stimulation based on analyzing the results of signals generated by the example apparatus and methods. Instead of detecting or recording seizure activity as a function of signals generated by the brain, example apparatus and methods monitor the response(s) generated by stimulation. For example, a stimulation may be produced and the amplitude of the response generated by the stimulation may be measured. When no seizure is imminent, the amplitude of the response generated by the stimulation may fall within a first range. When a seizure is imminent, the amplitude of the response generated by the stimulation may fall within a second different range. When the response generated by the stimulation falls within the second, different range, example apparatus and methods may control the stimulation to mitigate or prevent a seizure. In another embodiment, the frequency content may have specific characteristics that differ before the seizure is imminent from when the seizure is not imminent. In another embodiment, the shape of the evoked response measured by conventional signal processing technique (e.g., half-width duration, rise/fall time) may vary before a seizure is imminent from when it is not imminent. The amplitude, frequency content, shape, or other property of the response may be a function of properties of tissue in the target area that are affected by a seizure precursor.

Conventional systems may have attempted to detect an impending epileptic seizure based on signals generated in the brain by the brain. Example apparatus and methods apply low frequency stimulation to a stimulation site (e.g., hippocampal commissure) to cause an evoked potential in one or more target areas. The potential that is evoked in a target area may depend, at least in part, on whether a seizure is imminent Bio-chemical or bio-electrical changes associated with an impending seizure may cause the evoked potential to vary. The signal being examined to determine whether a seizure is imminent is a signal produced in response to stimulation, it is not a naturally occurring signal.

In one example, the amplitude of a response evoked in a target region is monitored and may be recorded. The amplitude of the response may vary based on the excitability of the tissue. For example, when a seizure is imminent, the excitability of the tissue may increase. If the excitability increases then the amplitude of the evoked response may also increase. Example apparatus and methods may monitor the amplitude of the evoked response and selectively alter the stimulation provided to the stimulation site (e.g., white matter tract, FDC, hippocampal commissure) as a function of the detected amplitude.

In another example, the monitoring or recording electrode may be used to monitor the impedance of the tissue in the target region. A low amplitude signal may be passed into the tissue around the electrode and the impedance measured. The low amplitude signal may be, for example, a sinusoidal signal. When a seizure is imminent, the impedance may change in a detectable way. When the change in impedance is detected, the stimulation provided may be selectively altered to mitigate or prevent the seizure. Once again, rather than rely on signals that are being generated organically in the brain, example apparatus and methods may generate signals that produce different measurable results when a seizure is imminent. Characteristics or properties of the stimulation (e.g., waveform, frequency) may be varied as a result of the different measurable results.

In one embodiment, the response evoked by stimulation signals (e.g., electrical waveforms) that are generated by example apparatus and methods may be analyzed with respect to frequency content or time properties. These signals include the evoked potential generated directly by a stimulus as well as the after-discharge observed following the evoked response. These evoked responses may be monitored or recorded from implanted electrodes or surface electroencephalography (EEG) electrodes. For example, the response evoked may have a first frequency content when no seizure is imminent but may have a second, different frequency content when a seizure is imminent. Similarly, the response evoked may have a first time property when no seizure is imminent but may have a second, different time property when a seizure is imminent. The time property may be, for example, how long it takes to evoke the response, the length of the evoked response, or other time-related properties.

Table 1 shows results of a study performed on subjects with intractable epilepsy who were implanted with depth electrodes as part of a surgical evaluation. There was no overt hippocampal pathology, including hippocampal sclerosis, on their brain MRIs. The seizure semiology and scalp-recorded interictal epileptiform discharges and ictal EEG suggested MTLE in all subjects.

Since neuropsychological testing found normal or only mildly-decreased memory scores, depth electrode evaluation was recommended to rule out an extra-hippocampal seizure onset, which would spare the non-lesional hippocampus surgically, thus preserving memory. Therefore, implanted areas included the temporal neocortex, amygdala, and hippocampus, in addition to areas known to be connected with the mesial temporal structures. The choice of these areas was guided partly by the seizure semiology, and included the insula in some subjects, temporal pole in some subjects, and the posterior cingulate gyrus in some subjects. In addition, depth electrodes were implanted in the basal temporal, frontal, and temporo-occipital areas in smaller subsets of subjects. The fornix electrodes were implanted in the corpus of the fornix in some subjects, and in an area that is anterolateral to the splenium of the corpus callosum where the crux of the fornix travels with fibers of the dorsal hippocampal commissure (the forno-dorso-commissural tract) in other subjects. The total number of electrodes to be implanted was decided according to clinical criteria. For research purposes, the trajectory of a single clinically-indicated electrode probe that sampled the temporoparietal or temporo-occipital cortex was modified to target the fornix medially.

After brain MRIs were obtained in the Leksell frame, the images were exported to the iPlan workstation (Brainlab, Inc. Westchester, Ill., USA) where electrode implantation was planned. The implantation targets were chosen and the coordinates were determined before the electrodes were advanced through drill twists to the target points under fluoroscopic guidance. The electrodes were platinum-iridium cylinders measuring 1.1 mm in diameter and 2.3 mm in length, evenly spaced at 5 mm intervals, and depth electrode probes contained 10-12 contacts (Adtech, Racine, Wis., USA). Other electrodes may be employed.

Following electrode implantation, the subjects were transferred to the Epilepsy Monitoring Unit and underwent continuous video-EEG monitoring. A head CT scan was obtained post-operatively and the locations of the depth electrodes were verified by co-registration of pre-surgical volumetric brain MRI with postsurgical volumetric brain CT (Brainlab, Inc. Westchester, Ill., USA) according to anatomical fiducials, as shown in FIG. 1. EEG recordings were made using Nihon Kohden (Foothill Ranch, Calif., USA). EEG channels were amplified, filtered (0.1-300 Hz), and recorded digitally with a sampling frequency of 1000 Hz.

The connectivity of the fornix with the hippocampus and posterior cingulate region was confirmed by applying single pulse electrical stimulation to the fornix and averaging the evoked responses in other regions. The pulses consisted of bipolar square waves applied to two contiguous electrodes with a pulse width of 0.2 msec at a current intensity of 8 mA/phase and a frequency of 1 Hz. Fifty pulses per electrode pair were applied and the evoked potentials were averaged. The raw EEG was initially visualized to exclude stimuli that included artifacts. Both bipolar and referential montages were used to display the averaged responses in order to confirm the consistency of the responses.

The Folstein mini-mental status examination (MMSE) was performed in all subjects before stimulation was started. Four of the subjects had another baseline MMSE score documented in their charts 2-6 months before electrode implantation. During the first four-hour stimulation session, a neurologist was present to monitor the EEG for seizures and after-discharges and perform hourly neurological assessment, including MMSE, for a total of three assessments per subject. Each assessment used a new set of three words to test registration and delayed recall. Each set of words consisted of a state name in the U.S., a color, and an abstract quality, such as 'honesty'. All dosages of antiepileptic drugs (AEDs) administered during the hospital stay were recorded, and subjects who received AEDs less than two days prior to stimulation were excluded from the seizure analysis.

Fornix stimulation was performed using bipolar square waves with a pulse width of 0.2 msec, current intensity of 8 mA/phase, and stimulation frequency of 5 Hz in all subjects. At 8 mA/phase, the charge density was 20 microcoulombs ($\mu$C) per square centimeter, which is below the safe maximum. Stimulation occurred in four-hour sessions. Some subjects underwent one four-hour stimulation session, some subjects underwent three sessions over three days, some subjects had two sessions over two days, and some subjects underwent nine sessions. For the subjects who had hippocampal seizure onset, the entire continuous EEG starting 1-2 days before the first low frequency stimulation session and ending 1-2 days after the last session was then reviewed, and the hippocampal spikes were counted and documented per hour of the day. These subjects' seizure times were also documented in order to study the effect of low frequency stimulation on seizures.

Generalized estimating equations (GEE) models were used to estimate the impact of stimulation on seizure count and spike count. An exchangeable correlation matrix structure was used for outcomes to indicate that the degree of similarity within subjects was comparable across subjects. The logit link function was used for seizure count, which is a binomial variable (presence versus absence), and the identity link function for spike count and MMSE scores, since these are continuous variables. Seizure counts were analyzed using seizures per four hour block in the 24-48 hours that preceded the first stimulation session and the same duration that followed the last session for some subjects. Model coefficients for seizure count analysis were exponentiated to yield an odds ratio that approximated the relative likelihood of seizures during and after stimulation versus before stimulation. Thus, "seizure odds" refers to a ratio describing the relative likelihood of a seizure during and after stimulation versus before stimulation. Model coefficients for spike count and MMSE analysis were interpreted as change in numbers from 'during' versus 'before' stimulation, that is, a negative coefficient would indicate reduction. The Mann-Whitey U test was used to analyze the MMSE scores.

The hippocampal evoked responses to fornix stimulation showed an early negative deflection with a mean latency of 37±11 msec in all subjects. Subsequent components were seen less consistently. The initial response for some patients had a bifid morphology with the first negative peak occurring between 24 and 37 msec, and the second negative peak occurring within 20 msec of the first peak. In other patients, a slow negative response peaked between 150 and 166 ms. Some subjects had a later negative bifid response with one peak at 200-229 and another at 241-250 msec. In addition, one subject had a reverberating rhythm with additional negative peaks at 300, 360, and 420 msec.

For the clinical purposes of ruling out seizure onset in regions with known connectivity with the mesial temporal lobe, some subjects underwent implantation of depth electrodes in the posterior cingulate gyrus, and postoperative imaging confirmed electrode localization in that region. Stimulation of the fornix at 1 Hz resulted in evoked responses in the posterior cingulate gyms in all subjects. In some subjects, these responses consisted of a late positive response at 187 msec. In one subject, initial small negative peaks at 27 and 56 msec were followed by a late negative peak at 200 msec. The posterior cingulate response had a latency of 70 msec in the remaining two subjects, and was of positive polarity in one subject and negative in another subject.

No seizures occurred during low frequency stimulation in patients with hippocampal epilepsy, but some seizures occurred during stimulation in patients with extra-hippocampal epilepsy. Some subjects had additional documented MMSE scores before implantation. In these subjects, the pre-implantation and post-implantation baseline scores were not different (p=0.44). Data was entered into a GEE model that accounted for intra-individual and inter-individual differences. The results showed that stimulation produced a significant increase in the MMSE score of 0.82 points (P<0.001).

Analyzing the delayed recall component of the MMSE showed that out of three possible points, the average pre-stimulation score in the subjects was 1.53±0.92, which increased to 2.27±0.67 during stimulation. Thus, the MMSE score improvement was largely due to improvement of the delayed recall component. Comparing the baseline recall score that was obtained after electrode implantation with the first recall score obtained one hour through stimulation revealed no significant difference (p=0.26), but comparing the baseline with second and third recall scores obtained during stimulation showed a significant increase (p=0.038 and 0.01, respectively).

Figure 3:
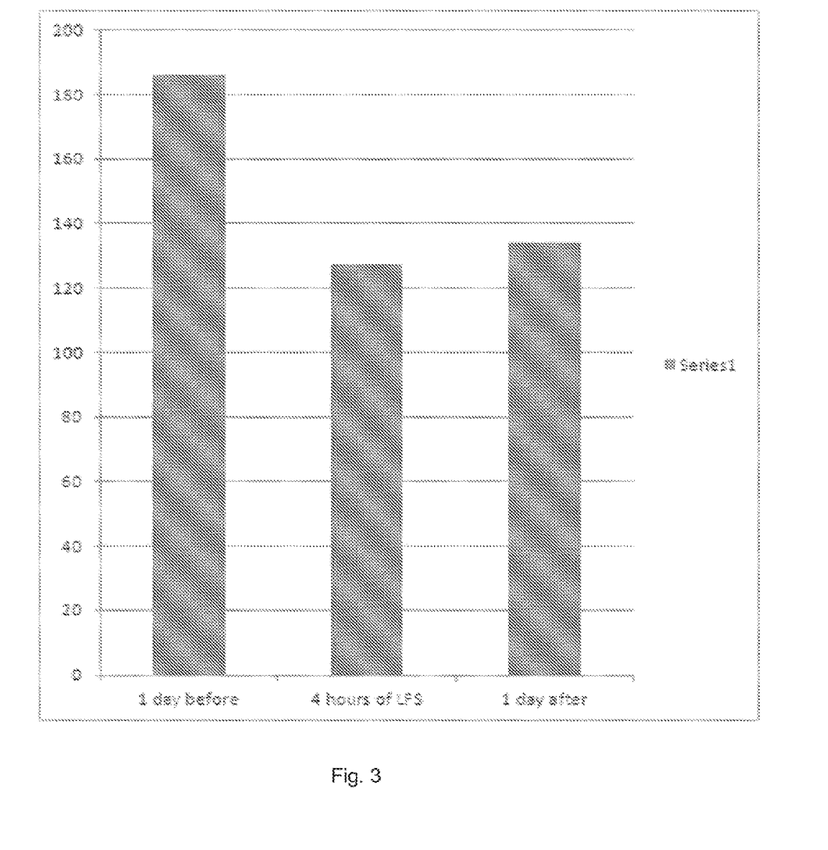
FIG. 3 illustrates hippocampal spike counts averaged per hour before, during, and after low-frequency stimulation.

FIG. 3 illustrates hippocampal spike counts averaged per hour before, during, and after low-frequency stimulation. The spike count is reduced during and even after low-frequency stimulation. The reduction in spike count indicates the reduction of hyper-excitability of neural tissue. Overall, a reduction of hippocampal spikes by 36.4 spikes/hour (95% confidence interval of spike reduction 15.8-56.9, p=0.001), from a baseline of 58.1 spikes/hour to 21.7 spikes/hour was achieved during stimulation. The spike reduction persisted for the subsequent four hours (p=0.05), before returning to baseline.

Figure 4:
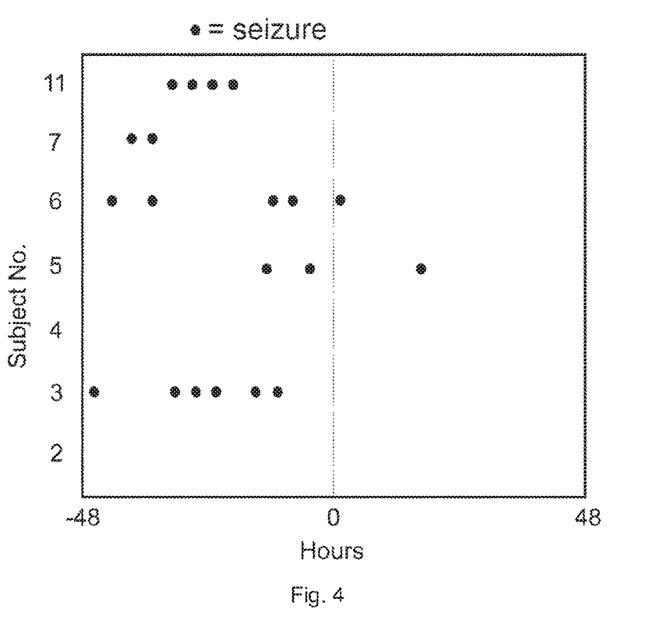
FIG. 4 illustrates a scatter plot showing seizures recorded before and after example stimulation.

The seizure analysis included the period around stimulation where antiepileptic medications were not changed (n=7, Table 1, FIG. 4). FIG. 4 illustrates a scatter plot showing the seizures recorded before and after stimulation. In FIG. 4, zero hour corresponds to the time during which low frequency stimulation of the fornix was in progress. The seizure counts included represent the number of seizures in the forty eight hours that preceded the first session (−48, 0), and the number of seizures that followed the last session (0, 48). No seizures occurred during stimulation. The number of seizures after stimulation was reduced. Seizure odds were reduced by 90.3% for up to two days following stimulation.

Stimulation of a white matter tract can interfere with the spontaneous activity of a relatively broader brain region. The fornix is a compact white matter tract and may be stimulated using one or more electrodes, which will synchronize, and may override spontaneous activity across the length of the hippocampus as evidenced by the robust, short-latency evoked responses recorded from the hippocampus. Direct stimulation of the hippocampus at both high (e.g., >10 Hz) or low (e.g., <1 Hz) frequencies can impair memory. However, stimulation of extra-hippocampal structures within the memory circuit, such as the fornix or the entorhinal cortex, may enhance memory. This is associated with activity-dependent regulation of hippocampal neurogenesis. Such effects have been observed with high-frequency stimulation of the entorhinal cortex and other limbic targets such as the anterior thalamic nucleus.

Low frequency stimulation is attractive for clinical implementation since the duty cycle of the stimulation is low, implying less electric current injection with less charge density on target tissue and electrodes and longer battery life. In one embodiment, when a seizure focus is identified, a white matter tract that is intimately connected to that focus may be identified (e.g., through tractography) and stimulated. As an example, seizure foci in perisylvian language areas can be treated by low frequency stimulation of parts of the arcuate fasciculus. In another embodiment, a closed-loop, feedback stimulation detects and aborts hippocampal seizure episodes without inducing adverse effects of continuous stimulation.

Some portions of the detailed descriptions that follow are presented in terms of algorithms and symbolic representations of operations on data bits within a memory. These algorithmic descriptions and representations are used by those skilled in the art to convey the substance of their work to others. An algorithm is considered to be a sequence of operations that produce a result. The operations may include creating and manipulating physical quantities that may take the form of electronic values. Creating or manipulating a physical quantity in the form of an electronic value produces a concrete, tangible, useful, real-world result.

It has proven convenient at times, principally for reasons of common usage, to refer to these signals as bits, values, elements, symbols, characters, terms, numbers, and other terms. It should be borne in mind, however, that these and similar terms are to be associated with the appropriate physical quantities and are merely convenient labels applied to these quantities. Unless specifically stated otherwise, it is appreciated that throughout the description, terms including processing, computing, and determining, refer to actions and processes of a computer system, logic, processor, or similar electronic device that manipulates and transforms data represented as physical quantities (e.g., electronic values).

Example methods may be better appreciated with reference to flow diagrams. For simplicity, the illustrated methodologies are shown and described as a series of blocks. However, the methodologies may not be limited by the order of the blocks because, in some embodiments, the blocks may occur in different orders than shown and described. Moreover, fewer than all the illustrated blocks may be required to implement an example methodology. Blocks may be combined or separated into multiple components. Furthermore, additional or alternative methodologies can employ additional, not illustrated blocks.

Figure 7:
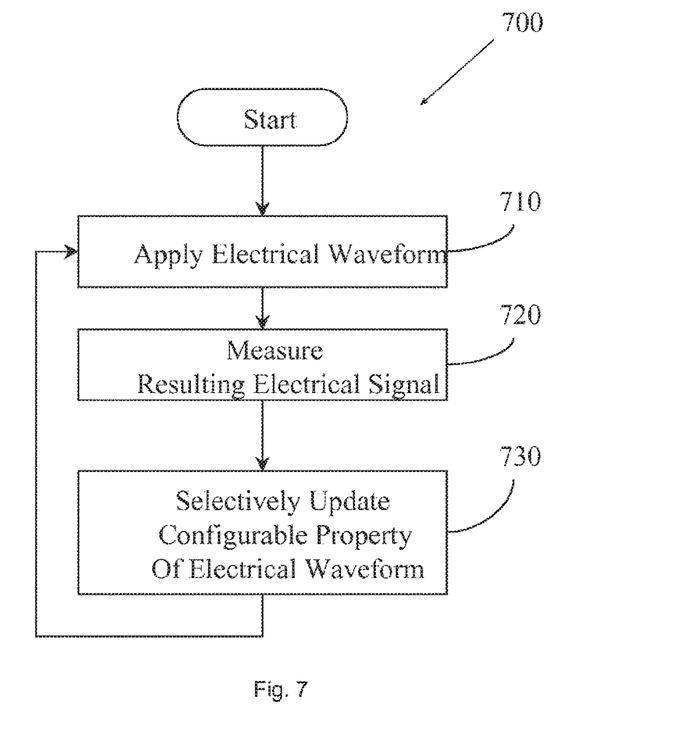
FIG. 7 illustrates an example method associated with achieving a desired therapeutic effect by controlling stimulation of the FDC based on the signal evoked in response to stimulating the FDC.

FIG. 7 illustrates a method 700 associated with configuring a neuro-stimulation signal based on a desired therapeutic effect and the response the stimulation produced by applying the neuro-stimulation signal evokes in a targeted area. Method 700 may include, at 710, applying an electrical waveform with a low frequency (e.g., less than 10 Hz) to white matter in a human brain using an implanted electrode. In one embodiment, the white matter is the forno-dorso-commissure (FDC). The FDC is an area anterolateral to the splenium of the corpus callosum where the crux of the fornix travels with fibers of the dorsal hippocampal commissure. In one embodiment, the implanted electrode is a single electrode implanted unilaterally. In another embodiment, the implanted electrode may be two electrodes implanted bilaterally.

In one embodiment, the electrical waveform is applied according to one or more configurable properties. The configurable properties may include, for example, the frequency at which the electrical waveform is applied. In one embodiment, the frequency may be 10 Hz or less. In another embodiment, the frequency may be 2 Hz or less. Different frequencies may be employed. The one or more configurable properties may also include, for example, the type of waveform, the pulse width, the current intensity, the current amplitude, the voltage amplitude, or other properties. In one example, the waveform is a sinusoidal waveform. In another example, the waveform is a bipolar square wave with a pulse width between 0.1 msec and 0.3 msec, a current intensity between 5 mA/phase and 10 mA/phase, and a voltage amplitude between 1V and 10V.

Method 700 may also include, at 720, measuring a resulting electrical signal in a target area in the brain. The target area is connected to the white matter, innervated by the white matter, or can be activated by the white matter. For example, when the area stimulated is the FDC, the target area may be the hippocampus, the posterior cingulate gyms, or the amygdala. Other target areas may be employed. The resulting electrical signal is produced in response to applying the electrical waveform to the white matter.

Various properties of the resulting electrical signal may be measured. Thus, measuring the resulting electrical signal at 720 may include measuring the amplitude of the electrical signal, measuring the frequency content of the electrical signal, measuring the shape of the electrical signal, or measuring a time property of the electrical signal. The resulting electrical signal may have different properties at different times. Thus, in one embodiment, measuring the electrical signal occurs between 50 ms and 250 ms after the end of the application of the electrical waveform. In different embodiments, the electrical signal may be measured using an implanted electrode or surface EEG electrode.

Method 700 may also include, at 730, selectively updating a member of the one or more configurable properties until applying the electrical waveform produces a desired electrical signal. In one embodiment, producing the desired electrical signal reduces hyper-excitability of neural tissue in the target area. Reducing hyper-excitability may in turn reduce hippocampal spikes, reduce seizures, or reduced other undesired events.

In one embodiment, method 700 may include computing an impedance of tissue in the target region based on the electrical signal. The one or more configurable properties may then be updated based on the impedance.

The electrical waveform may be configured and applied to achieve different results or therapeutic effects. In one example, the electrical waveform may be configured and applied to produce an electrical signal that will reduce hyper-excitability of neural tissue in the target area in an amount sufficient to prevent an epileptic seizure. In one embodiment, the electrical waveform may be configured and applied to produce an electrical signal that prevents an epileptic seizure originating in the mesial temporal lobe.

The stimulation provided by the electrical waveform may be configured and reconfigured to produce an electrical signal that reduces hippocampal spikes by at least ten spikes per hour. Different waveforms may be produced to reduce hippocampal spikes by other amounts. Reducing hyper-excitability of neural tissue in a target region may reduce seizure odds by at least ninety percent. The stimulation may produce results during a stimulation session and even after a stimulation session. In one embodiment, the electrical waveform may be configured and applied to produce an electrical signal that reduces hippocampal spikes by at least fifty percent while the method is being performed. In another embodiment, the method may be performed for a time period sufficient to produce a carryover effect that reduces hyper-excitability of neural tissue in the target area after the method is no longer being performed. In different embodiments, the carryover effect may last for four hours, twenty four hours, or even longer.

In one embodiment, the stimulation may be targeted at recall. Thus, in one embodiment, the electrical waveform may be configured and applied to reduce hyper-excitability of neural tissue in the target area in an amount sufficient to improve recall in patients having Alzheimer's, hippocampal sclerosis, autism, schizophrenia, senile dementia, or stroke.

While FIG. 7 illustrates various actions occurring in serial, it is to be appreciated that various actions illustrated in FIG. 7 could occur substantially in parallel. By way of illustration, a first process could control applying stimulation, a second process could monitor or record evoked potentials, and a third process could reconfigure stimulation parameters based on the evoked potentials and a desired therapeutic effect. While three actions are described, it is to be appreciated that a greater and/or lesser number of actions could be employed.

Figure 8:
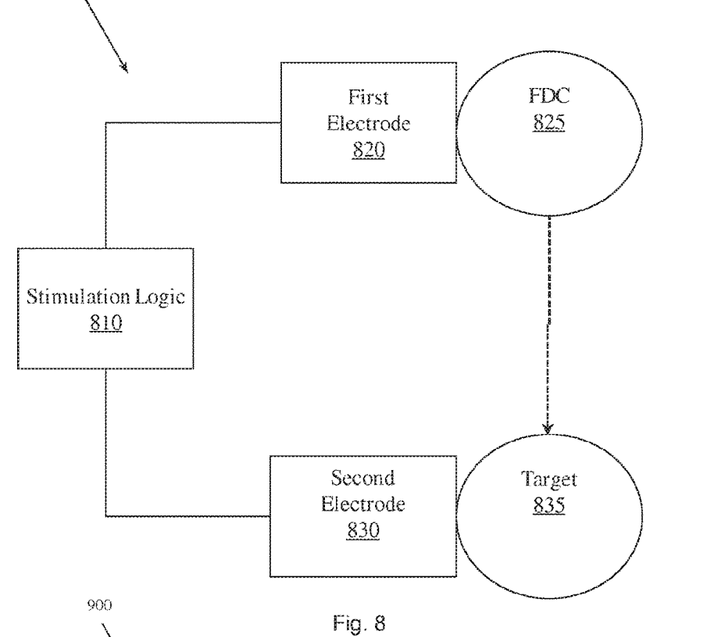
FIG. 8 illustrates an example apparatus associated with achieving a desired therapeutic effect by controlling stimulation of the FDC based on the signal evoked in a target area in response to stimulating the FDC.

FIG. 8 illustrates an apparatus 800. Apparatus 800 includes a stimulation logic 810 that is configured to control the application of a neuro-stimulation signal to the forno-dorso-commissure (FDC) 825 during a stimulation session. In one embodiment, the stimulation logic 810 controls the application of the neuro-stimulation signal to the FDC 825 based, at least in part, on a characteristic of the electrical signal and on a desired therapeutic effect. Thus, a feedback loop may be set up where the stimulation logic 810 produces an effect at the target 835, the effect is analyzed, and the stimulation logic 810 is reconfigured based on the analysis.

The stimulation logic 810 may control the neuro-modulation signal with respect to frequency, amplitude, wave form, pulse width, current amplitude, voltage amplitude, or other properties. For example, the stimulation logic 810 may produce sinusoidal waves, square waves, or other waveforms having different frequencies, amplitudes, and pulse widths.

Apparatus 800 also includes a first electrode 820 that is connected to the stimulation logic 810. The first electrode 820 may be configured to apply the neuro-stimulation signal to the FDC 825. While a single electrode 820 is illustrated, in one embodiment, stimulation logic 810 may provide a neuro-stimulation signal to two or more electrodes. In one embodiment, the neuro-modulation signal has a frequency of less than five hertz. Other frequencies may be employed.

Apparatus 800 also includes a second electrode 830 that is connected to the stimulation logic 810. The second electrode 830 is configured to detect an electrical signal evoked in a target neural tissue 835 in response to the application of the neuro-stimulation signal. The target neural tissue 835 is connected to, innervated by, or can be activated by the FDC. The target neural tissue 835 may be, for example, the hippocampus, the posterior cingulate gyrus, or the amygdala. Other targets may be employed. While a single electrode 830 is illustrated, one or more electrodes may monitor or record potentials evoked in the target 835.

The characteristic of the electrical signal evoked in the target neural tissue may be analyzed with respect to, for example, amplitude, frequency, frequency content, shape, a time at which the electrical signal was detected, or a length of time during which the electrical signal was detected. Different desired therapeutic effects may be achieved when different characteristics of the electrical signal fall within certain ranges or have certain properties.

The therapeutic effects may be related to a property of the tissue (e.g., hyper-excitability), an effect noticed in a portion of the brain (e.g., hippocampal spikes), or an over-arching effect (e.g., seizure). Thus, in one example, the desired therapeutic effect is a ten percent reduction in hyper-excitability of the target neural tissue. Other reductions may be sought. In another example, the desired therapeutic effect is a fifty percent reduction in hippocampal spikes. Other reductions may be sought. In yet another example, the desired therapeutic effect is reducing seizure odds by seventy five percent. Other reductions may be sought. In yet another embodiment, the desired therapeutic effect is improving memory recall in a patient having Alzheimer's, hippocampal sclerosis, autism, schizophrenia, senile dementia, or stroke.

The stimulation logic 810 may provide stimulation during a stimulation session and a desired therapeutic effect may be achieved during the stimulation session. In one embodiment, the stimulation logic 810 may be configured to cause the neuro-stimulation signal to be applied to the FDC 825 for a period of time sufficient to produce the therapeutic effect after the stimulation session has ended.

Figure 9:
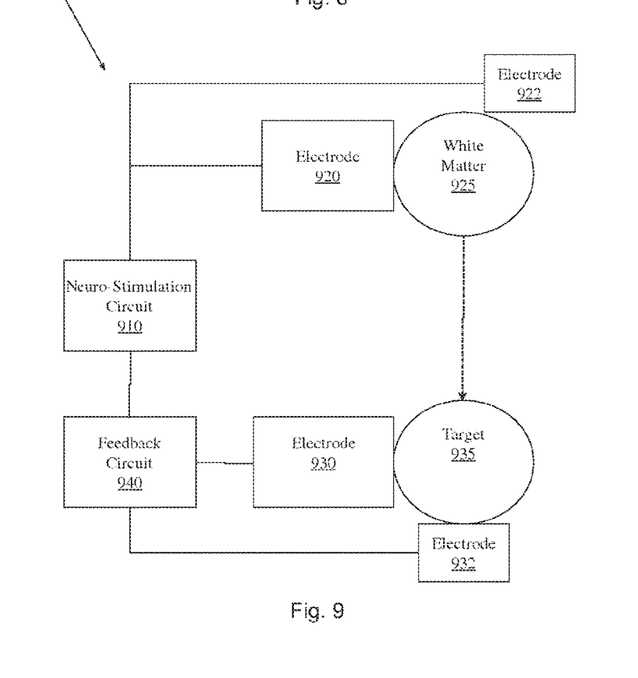
FIG. 9 illustrates an example apparatus associated with achieving a desired therapeutic effect by controlling stimulation of the FDC based on the signal evoked in a target area in response to stimulating the FDC.

FIG. 9 illustrates an apparatus 900. Apparatus 900 includes a neuro-stimulation circuit 910 that is configured to produce a dynamically re-configurable neuro-stimulation signal having a frequency of less than 2 Hz. Apparatus 900 also includes one or more neuro-stimulation electrodes (e.g., electrode 920, electrode 922) that are implanted unilaterally or bilaterally and configured for applying the neuro-stimulation signal to white matter 925 (e.g., forno-dorso-commissure (FDC)).

Apparatus 900 also includes one or more monitoring electrodes (e.g., electrode 930, electrode 932) that are configured to detect an electrical potential evoked in a target neural tissue 935 in response to the neuro-stimulation signal being applied to the white matter 925. Since apparatus 900 intends to reconfigure the neuro-stimulation circuit 910 based on a potential evoked by applying the neuro-stimulation signal to the white matter 925, the target neural tissue 935 is connected to, innervated by, or can be activated by the white matter 925.

Apparatus 900 also includes a feedback circuit 940 that is configured to control the neuro-stimulation circuit 910. The neuro-stimulation circuit 910 is controlled based on the detected electrical potential and a desired therapeutic effect. The feedback circuit 940 controls the neuro-stimulation circuit 910 to dynamically reconfigure the neuro-stimulation signal.

TABLE 1

| Subject No. | Handedness | Age | Age at Seizure Onset | Seizure Focus Localization | Seizure Semiology |
|---|---|---|---|---|---|
| 1 | Right | 34 | 1 | Right hippocampus | Epigastric sensation, alteration of awareness with automatisms |
| 2 | Right | 56 | 46 | Left hippocampus | Epigastric sensation, alteration of awareness |
| 3 | Right | 23 | 14 | Left hippocampus | Psychic aura, alteration of awareness with automatisms |
| 4 | Right | 38 | 35 | Right hippocampus | Psychic aura, gustatory experience, alteration of awareness |
| 5 | Right | 51 | 19 | Left hippocampus | Alteration of awareness with automatisms |
| 6 | Right | 28 | 22 | Right hippocampus | Cephalic aura, alteration of awareness, left version |
| 7 | Right | 39 | 29 | Left hippocampus | Alteration of awareness with automatisms, right version |
| 8 | Ambidextrous | 46 | 17 | Left temporal neocortex | Psychic aura, aphasic seizure |
| 9 | Right | 37 | 1 | Extrahippocampal | Cephalic aura, alteration of awareness |
| 10 | Right | 39 | 19 | Extrahippocampal | Cephalic aura, alteration of awareness with automatisms |
| 11 | Right | 55 | 30 | Right hippocampus | Psychic aura, alteration of awareness with automatisms |

| Subject No. | Brain MRI Findings | WMS - verbal delayed | WMS - visual delayed | Intracarotid Amobarbital Procedure | Days before first, and after last, stimulation with no AED changes | Days before first, and after last, stimulation included in spike and seizure analysis |
|---|---|---|---|---|---|---|
| 1 | Normal | 120 | 72 | Left Language and memory | −1, 2 | −1, 1↑ |
| 2 | Normal | 102 | 115 | Left Language, bilateral memory | −8, 9 | −2, 2 |
| 3 | Normal | 108 | 103 | — | −2, 2 | −2, 2 |
| 4 | Normal | 124 | 132 | — | −4, 1 | −1, 1 |
| 5 | Non-specific white matter changes | 71 | 84 | Left Language, bilateral memory | −5, 1 | −1, 1 |
| 6 | Normal | 99 | 94 | Left | −1*, 4 | −2, 2 |

TABLE 1-continued

| | | | | | | |
|---|---|---|---|---|---|---|
| 7 | Normal | 83 | 78 | Left Language, bilateral memory | −2, 2 | −2, 2 |
| 8 | Left hippocampus is smaller than the right hippocampus, without signal changes | 99 | 115 | Left Language, bilateral memory | −1, 2 | |
| 9 | Increased T2 signal within the middle and posterior hippocampus bilaterally | 77 | 81 | Left Language, bilateral memory | −3, 1 | |
| 10 | Non-enhancing left entorhinal and amygdala T2/FLAIR hyperintensity | 94 | 109 | Left Language, bilateral memory | −1, 1 | |
| 11 | Normal | 94 | 97 | Left Language, bilateral memory | −3*, 4 | −2, 2 |

WMS, Wechsler Memory Scale
AED, antiepileptic drug
*An AED was discontinued
† Included in spike, but not seizure analysis The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and other similar exemplary language indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and other entities. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"Signal", as used herein, includes but is not limited to, electrical signals, optical signals, analog signals, digital signals, data, computer instructions, processor instructions, messages, a bit, a bit stream, and other items, that can be received, transmitted and/or detected.

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the embodiments described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AAA, AAB, AABB, AABBC, AABBCC, (e.g., the data store may store only A, only B, only C, A&B, A&C, B&C, A&B&C, A&A&A, A&A&B, A&A&B&B, A&A&B&B&C, A&A&B&B&C&C). It is not intended to require one of A, one of B, and one of C. When the applicants intend to indicate "at least one of A, at least one of B, and at least one of C", then the phrasing "at least one of A, at least one of B, and at least one of C" will be employed.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

Having described the invention what is claimed is:

1. A method comprising:
    applying an electrical stimulation signal with a frequency of less than 10 Hz to a white matter tract in the brain for a time; and
    reducing hyper-excitability of a target neural tissue that is activated by the white matter tract,
    wherein the hyper-excitability is reduced as a carryover therapeutic effect for at least four hours after the time.

2. The method of claim 1, wherein the white matter tract comprises the forno-dorso-commissure (FDC).

3. The method of claim 1, wherein the electrical stimulation signal is applied according to one or more configurable properties by an implanted stimulating electrode.

4. The method of claim 3, further comprising updating the one or more configurable properties to reduce the hyper-excitability of the target neural tissue.

5. The method of claim 3, wherein the one or more configurable properties comprise at least one of a type of waveform, a pulse width, a current intensity, a current amplitude, and a voltage amplitude.

6. The method of claim 5, wherein the updating is based on a feedback signal that indicates the hyper-excitability of the target neural tissue.

7. The method of claim 6, wherein the feedback signal indicates an impedance of the target neural tissue,
    wherein the impedance correlates to the hyper-excitability of the target neural tissue.

8. The method of claim 1, wherein the target neural tissue comprises at least a portion of the hippocampus, the posterior cingulate gyrus, or the amygdala.

9. The method of claim 1, wherein the hyper excitability is indicative of seizure behavior.

10. The method of claim 1, wherein a duty cycle associated with the electrical stimulation signal is low such that a small amount of electric current is injected into the target tissue.

11. A system comprising:
    a stimulation generator to generate an electrical stimulation signal with a frequency of less than 10 Hz; and
    at least one electrode to apply the electrical stimulation signal to a white matter tract in the brain for a time; and
    wherein hyper-excitability of a target neural tissue that is activated by the white matter tract is reduced as a carryover therapeutic effect for at least four hours after the time.

12. The system of claim 11, wherein the white matter tract comprises the forno-dorso-commissure (FDC).

13. The system of claim 11, wherein the stimulation generator alters the electrical waveform in response to a change of one or more configurable parameters in response to a feedback signal that indicates the hyper excitability of the target neural tissue,
    wherein the change of the one or more configurable parameters reduces the hyper-excitability of the target neural tissue.

14. The system of claim 13, wherein the one or more configurable parameters comprise at least one of a type of waveform, a pulse width, a current intensity, a current amplitude, and a voltage amplitude.

15. The system of claim 13, wherein the feedback signal indicates an impedance of the target neural tissue,
    wherein the impedance correlates to the hyper-excitability of the target neural tissue.

16. The system of claim 11, wherein the target neural tissue comprises at least a portion of the hippocampus, the posterior cingulate gyrus, or the amygdala.

17. The system of claim 11, wherein the hyper excitability is indicative of seizure behavior.

18. The system of claim 11, wherein the stimulation generator further comprises a feedback circuit to receive a feedback signal from at least one recording electrode.

19. The system of claim 18, wherein the at least one recording electrode comprises an implanted electrode or an external electrode.

20. The system of claim 11, wherein the electrical stimulation signal has a frequency of less than 5 Hz.

* * * * *